(12) United States Patent
Samzelius

(10) Patent No.: US 10,694,987 B1
(45) Date of Patent: Jun. 30, 2020

(54) NEUROLOGICAL DISORDER DETERMINING AND MONITORING SYSTEM AND METHOD

(71) Applicant: Habit DX Inc., San Francisco, CA (US)

(72) Inventor: Jan Samzelius, San Francisco, CA (US)

(73) Assignee: NEURAMETRIX, INC., Hillsborough, CA (US)

( * ) Notice: Subject to any disclaimer, the term of this patent is extended or adjusted under 35 U.S.C. 154(b) by 831 days.

(21) Appl. No.: 14/318,477

(22) Filed: Jun. 27, 2014

Related U.S. Application Data

(60) Provisional application No. 61/840,001, filed on Jun. 27, 2013.

(51) Int. Cl.
*A61B 5/16* (2006.01)

(52) U.S. Cl.
CPC .................................. *A61B 5/162* (2013.01)

(58) Field of Classification Search
None
See application file for complete search history.

(56) References Cited

U.S. PATENT DOCUMENTS

| | | | |
|---|---|---|---|
| 4,805,222 A | 2/1989 | Young et al. | |
| 5,557,686 A | 9/1996 | Brown | |
| 5,885,231 A * | 3/1999 | Cramer | A61B 5/1124 600/587 |
| 8,230,232 B2 | 7/2012 | Ahmed | |
| 8,346,680 B2 | 1/2013 | Castleman et al. | |
| 8,533,486 B1 | 9/2013 | Stark et al. | |
| 8,997,191 B1 | 3/2015 | Stark et al. | |
| 9,329,699 B2 | 5/2016 | Allen et al. | |
| 2002/0192624 A1 * | 12/2002 | Darby | A61B 5/16 434/236 |
| 2004/0059950 A1 | 3/2004 | Bender et al. | |
| 2004/0167380 A1 * | 8/2004 | Simon | A61B 5/16 600/300 |
| 2006/0195328 A1 | 8/2006 | Abraham et al. | |
| 2007/0234056 A1 | 10/2007 | Mani et al. | |
| 2008/0091639 A1 | 4/2008 | Davis et al. | |
| 2008/0092209 A1 | 4/2008 | Davis et al. | |
| 2008/0098456 A1 | 4/2008 | Alward et al. | |
| 2009/0002178 A1 | 1/2009 | Guday et al. | |
| 2012/0098750 A1 | 4/2012 | Allen et al. | |
| 2012/0235819 A1 | 9/2012 | Watkins et al. | |
| 2013/0176413 A1 | 7/2013 | Lowry et al. | |
| 2013/0326604 A1 | 12/2013 | Hird | |

(Continued)

FOREIGN PATENT DOCUMENTS

| | | |
|---|---|---|
| WO | WO2007/078756 | 7/2007 |
| WO | WO2012/128952 | 9/2012 |

OTHER PUBLICATIONS

Banerjee et al.; Biometric Authentication and Identification using keystroke Dynamics: A Survey; Journal of Pattern Recognition Research 7, 116-139 (2012).

(Continued)

*Primary Examiner* — Sean P Dougherty
*Assistant Examiner* — Benjamin S Melhus
(74) *Attorney, Agent, or Firm* — DLA Piper LLP (US)

(57) ABSTRACT

A system and method for determining and monitoring a neurological disorder using key action cadence is disclosed.

18 Claims, 6 Drawing Sheets

(56) References Cited

U.S. PATENT DOCUMENTS

| | | | |
|---|---|---|---|
| 2013/0338541 A1* | 12/2013 | Metman | A61B 5/1124 600/595 |
| 2013/0347099 A1 | 12/2013 | Smith | |
| 2014/0058241 A1 | 2/2014 | Apparies et al. | |
| 2015/0169854 A1 | 6/2015 | Chang et al. | |
| 2015/0296023 A1* | 10/2015 | Rokkaku | G06Q 50/24 709/203 |
| 2016/0345908 A1 | 12/2016 | Samzelius | |
| 2017/0116399 A1 | 4/2017 | Samzelius et al. | |
| 2017/0116405 A1 | 4/2017 | Samzelius et al. | |

OTHER PUBLICATIONS

H. Barghouthi; Keystroke Dynamics: How typing characteristics differ from one application to another; Masters Thesis: Master of Science in Information Security; Gjovik University College 67 pages (2009).

Clayton Epp et al.; Identifying emotional states using keystroke dynamics; Chi 2011 Session Emotional States 715-724 (2011).

Anil Jain et al.; Biometrics of Next Generation: An Overview: To Appear in Second Generation Biometrics' Springer 2010, 36 pages (2010).

Kevin Killourhy; A Scientific Understanding of Keystroke Dynamics: School of Computer Science Carnegie Mellon University: Thesis Committee: 213 pages (2012).

Kevin S. Killourhy et al. "Comparing Anomaly-Detection Algorithms for Keystroke Dynamics" Dependable Systems Laboratory, Computer Science Department, Carnegie Mellon University, 10 pages (2009).

Ryuhei Okuno et al. Finger Taps Movement Acceleration Measurement System for Quantitative Diagnosis of Parkinson's disease, Conference Proceedings . . . Annual International Conference of the IEEE Engineering in Medicine and Biology Society, 5 pages (Feb. 2006).

Information Security Stack Exchange; Authentication—Is behavioral analysis (e.g. keystroke dynamics) a reliable security mechanism for MFA? 5 pages (2013).

Signature and Keystroke Dynamics; Biometrics—The Hand-Signature and Keystroke Dynamics; 1 page (2013).

Esther Strauss et al. A Compendium of Neuropsychological Tests: Administration, Norms, and Commentary, Third Edition, Oxford University Press 1225 pages (2004).

J.R. Wall et al. "Can Motor Measures Tell us if Someone is trying? An Assessment of Sincerity of Effort in simulated malingering" Abstracts from the 18th Annual Meeting, 2 pages (1998).

Vizer, L. (2009) Detecting cognitive and physical stress through typing behavior. In Proceedings of ACM SIGCHI 2009 Conference on Human Factors in Computing Systems, Boston, MA 3113-3116, Apr. 2009.

Vizer et al. (2011). Detecting Cognitive impairment using keystroke and linguistic features of typed text: Toward an adaptive method for continuous monitoring of cognitive status. In Proceedings of Information Quality in e-Health—USAB 2011, Graz, Austria, Nov. 2011, A. Holzinger and K.M. Simonic Eds. Springer-Verlag, Lecture Notes in Computer Science 7058, 483-5000, 18 pages (2011).

Vizer, L. 2013. "Detecting cognitive impairment using keystroke and linguistic features of typed text. Toward an Adaptive Method for Continuous Monitoring of Cognitive Status",HFES 2013 Symposium on Human Factors and Ergonomics in Health Care: Advancing the Cause, 18 pages, (Mar. 2013).

Frid et al.; "Analysis of Finger Tapping Parameters in People with ADHD", dated 2012; IEEE 27-th Convention of Electrical and Electronics Engineers in Israel; (4 pgs.).

* cited by examiner

NEUROLOGICAL DISORDER DETERMINING AND MONITORING SYSTEM AND METHOD

PRIORITY CLAIMS/RELATED APPLICATIONS

This application claims the benefit and priority under 35 USC 119(e) to U.S. Provisional Patent Application Ser. No. 61/840,001, filed on Jun. 27, 2013, the entirety of which is incorporated herein by reference.

APPENDICES

Appendix A (14 Pages) is a portion of the key action data stream that may be provided to the backend component of the system for detecting and monitoring a neurological disorder.

Appendix B (1 page) is an example of a piece of text that was typed by a user that generated the portion of the key action data stream shown in Appendix A.

Appendices A and B form part of the specification.

FIELD

The disclosure relates generally to a system and method for determining and monitoring neurological diseases and/or neurological disorders.

BACKGROUND

When a neurological disease begins to affect a human body, few signs are noticeable that indicate that a particular human being has a neurological disease. Specifically, it may be years or even decades before the onset of otherwise observable symptoms. For example, the scientific community now thinks that the typical time between onset of the disease and diagnosable symptoms for Alzheimer's is 30 years. Research indicates that certain movement disorders are among the first symptoms of such neurological diseases. However, signs of movement disorders are difficult to observe and gather information on and uncertain in their predictive validity, until much later in the process of the disease.

Today, one particular method frequently used is the Finger Tapping Test (FTT). In its most common implementation, it is in essence a speed test. Patients are asked to tap with each index each of two levers, typically 20 centimeters apart, most often 5 times for each finger, at 10 seconds each time. Studies have shown that patients with brain disease perform more inconsistently on this test than control groups. More advanced versions of the FTT have included an analysis of consistency. Although the data is very limited, the findings indicate that consistency also declines with the onset of the disease.

The FTT test does deliver useful data, but it is very limited in its scope. Specifically, only two variables are measured (the number of taps during a 10/second period for each index finger). Typically, only 5 data points are captured for each variable (i.e. 5 10-second sessions) and each data point will be an integer between 20 and 70. One study has indicated that consistency is important, rather than speed and the FFT test delivers very limited consistency data. In the words of a major brain disease scientist: As we age, we get slower. But if we get more inconsistent, that is due to disease. The volume and granularity of FTT data is too low for early diagnosis. Also, since FTT requires in-person visits and special equipment, it is cumbersome and costly to use. Thus, FTT is not useful for detecting brain diseases early and accurately nor brain injuries on a continuous basis.

DETAILED DESCRIPTION OF ONE OR MORE EMBODIMENTS

The disclosure is particularly applicable to a typing device connected to a computing device that is used to gather data for detecting and monitoring a neurological disorder coupled to a backend system and it is in this context that the disclosure will be described. It will be appreciated, however, that the system and method has greater utility, such as to a standalone system that both gathers the data and analyzes the data, a standalone typing device that can be used to gather the data and the like.

The neurological disorder detection and monitoring system and method described below may dramatically increase the amount of data produced for detecting a neurological disorder using an activity most people do every day anyway—typing on a computer or like device—thus the measurement would not be intrusive and would be continuous and of much greater granularity and breadth. Thus, the system provides the medical community with many times more data and on an ongoing basis. The generated data is sub-clinical, thus different from FTT, in that the technology picks up very small changes as being statistically significant—changes so small neither the doctor, nor the patient, would ever be able to notice.

The neurological disorder detection and monitoring system and method may be used to gather data about and detect various neurological/neurological disorders including neurological diseases and brain injuries. More specifically, the neurological disorder detection system and method for any neurological diseases/injuries that may be measured/detected for diagnosis, drug efficacy and/or progression or recovery, using the neurological disorder detection system and method. For example, the neurological diseases may include, but are not limited to, Alzheimer's, Parkinson's, MS, Huntington's, ALS (Lou Gehrig's disease), Fronto-temporal dementia (FTD), Mild cognitive impairment (MCI), HIV Dementia, ADHD, post-operative neurological disorder and post-chemotherapy neurological disorder. For example, the brain injuries may include a traumatic brain injury (TBI), such as from car accidents, military activity, sports and the like.

Figure 1:
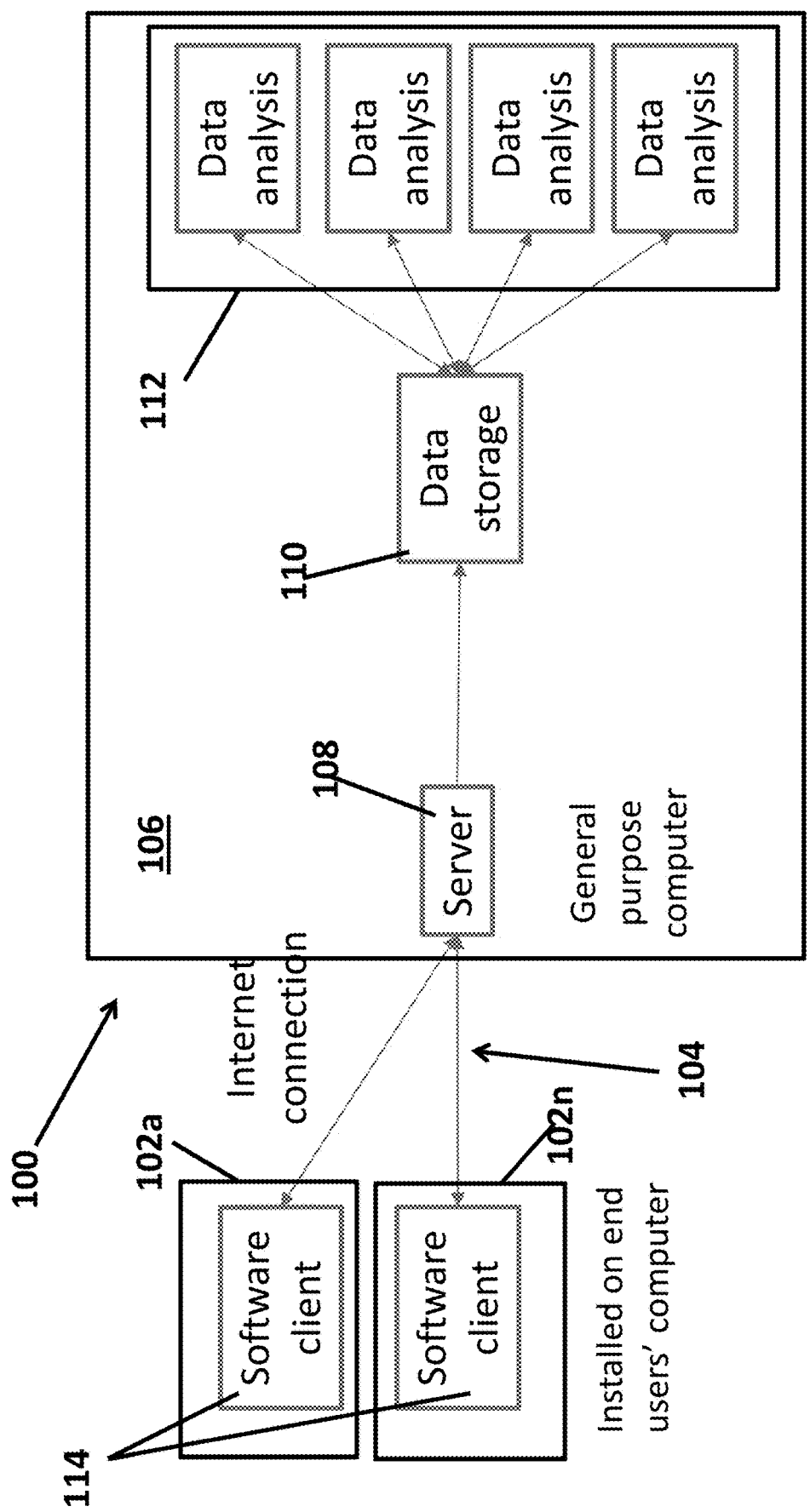
FIG. 1 illustrates an example of an implementation of a system for detecting and monitoring a neurological disorder.

FIG. 1 illustrates an example of an implementation of a system 100 for detecting and monitoring a neurological disorder. The system shown in FIG. 1 is implemented using a client server architecture, but the system may also be implemented as a cloud computing architecture, a standalone computer architecture or a software as a service (SaaS) model in which the typing cadence component, for example, may be downloaded to each computing device as needed. The system 100 may have one or more computing devices 102, such as computing device 102a, . . . , computing device 102n, each of which are connect to and communicate over a communications path 104 with a backend component 106. Each computing device 102 gathers, stores and communicates typing cadence data about a user who uses the computing device and the typing cadence data is sent over the communications path 104 to the backend component 106 that receives, stores and analyzes the typing cadence data to detect symptoms of a neurological disorder.

Each computing device may be a processor based system that has some input device so that the computing device is capable of collecting typing cadence data from the user as the user performs his daily tasks that includes typing on the input device. For example, each computing device may be a desktop computer, a laptop computer, a tablet computer, a smartphone, such as an Apple iPhone product or an Android Operating system (OS) based device, or a traditional mobile phone. The input devices for each computing device may include, for example, a built in keyboard, a detachable keyboard, a glass surface, a touchscreen, a virtual keyboard, a keypad, an electronically generated keyboard on a touchscreen and the like. Alternatively, each computing device may be a standalone device that captures typing cadence of a user. Each computing device may also have a typing cadence component 114 that may be resident on each computing device. The typing cadence component 114 may be a hardware circuit, a piece of software code, a hardware circuit programmed with a plurality of lines of computer code or an application. In the case of the typing cadence component 114 having software code or computer code, the typing cadence component 114 may be stored in a memory of the computing device and may be executed by a processor of the computing device 102.

The communications path 104 may be, as shown in FIG. 1, a public internet connection or a private network connection. Each computing device 102 may connect to the communications path using a known protocol and then connect to another system, such as the backend component and communicate with the backend component using a known protocol that may or may not be secure. For example, the communications path 104 may be a computer network, the Ethernet, the Internet, a digital data network, a wireless digital data network and the like. In one implementation, the communication path between each computing device and the backend component may be a standard internet connection (secure or public) while the communication path between the front end components 108 and the storage units 110 may be implemented using a dedicated, private connection.

The backend component 106 may include one or more front end components 108, one or more data stores 110 and one or more data analytics components 112 that are connected to each other as shown in FIG. 1. These components of the backend component may be implemented in hardware or software or a combination of hardware and software. In one implementation, the components are implemented in computing resources, such as one or more server computers or one or more cloud computing resources, that have at least a processor and a memory. In that implementation, each component may include a plurality of lines of computer code that may be stored in the memory and executed by the processor to provide the functions of each component that are described in more detail below with reference to FIG. 3.

In operation in one implementation, every user, patient or control, has the typing cadence component 114 installed on their computing device 102. The typing cadence component 114 hooks into the operating system and taps into the data stream from the input device and copies the clock time data for each key action/event. Each key action/event may be a the pressing of a key (key press) or a releasing of the key (a key release.) The typing cadence component 114 can store this information on the user's hard drive, but to greatly enhance security, the preferred embodiment is to store the data temporarily in a RAM of the computing device. The typing cadence component 114 may intermittently process the data, calculate all the differential timings used later in the process and packages a file it sends to the backend component 106. When the differential timings are calculated, as a security measure in some embodiments, the original clock stamps are removed—thus, the order of the characters is removed, making it impossible to put the data back to the original text.

An example of the key action data stream sent to the backend component 106 is contained in Appendix A that is incorporated herein by reference. Appendix A contains an example of a portion of the key action data stream for a particular user (serial number 1234.) As shown in the Appendix, the data may include first key identification data and second key identification data. Thus, for example "8" represents a particular key being pressed or released while "76" represents another key being pressed or released by the user. In one embodiment, the value for each key that identifies the key may be the well-known ASCII value for the particular key. The data also has one or more time samples (TS1, TS2, . . . , TS10, etc) that each happen during a time interval when and after the key combination action occurs. In one embodiment, each time sample may be measured in milliseconds. Each row in the data (other than the header row) represents a particular combination of first and second key actions and then time samples relevant to that particular combination of first and second key actions. When a particular row does not values for each sample period, the particular combination of first and second key actions has ended and no further key action data about that particular combination of first and second keys is available.

In the key action data in Appendix A, when the first and second key identifier are the same (such as in the first row), then the key action data represents a dwell time for the particular key (such as the key represented by the value "8") which is a time between a key press of the key and a release of the key by the user. As shown in the portion of the data, there are many different time samples for the dwell time for the key. In the key action data in Appendix A, when the first and second key identifier are different (such as "20" and "8" in the second row), then the key action data represents a flight time between a key press of the first key and a key press of the second key. As shown in the portion of the data, there are often fewer time samples for the flight time between the keys.

Thus, the typical cadence data from each computing device (and hence each user who uses that computing device) is captured and processed and used to, among other things, detect a possible neurological disorder of each user of each computing device. For example, the system may gather typing cadence data from users who do not have a neurological disorder and thus can compare the typing cadence data for a person without any neurological disorder to other users.

In operation, the backend component 106 may act as an organizer and may unpack the data file for each computing device, may determine to which user the particular computing device relates based on the file header of the particular data file, may convert the data from the format it was sent in into a common format, may calculate the profile data for the particular patient and may place the data and profile in the right folder in the data storage.

Figure 2:
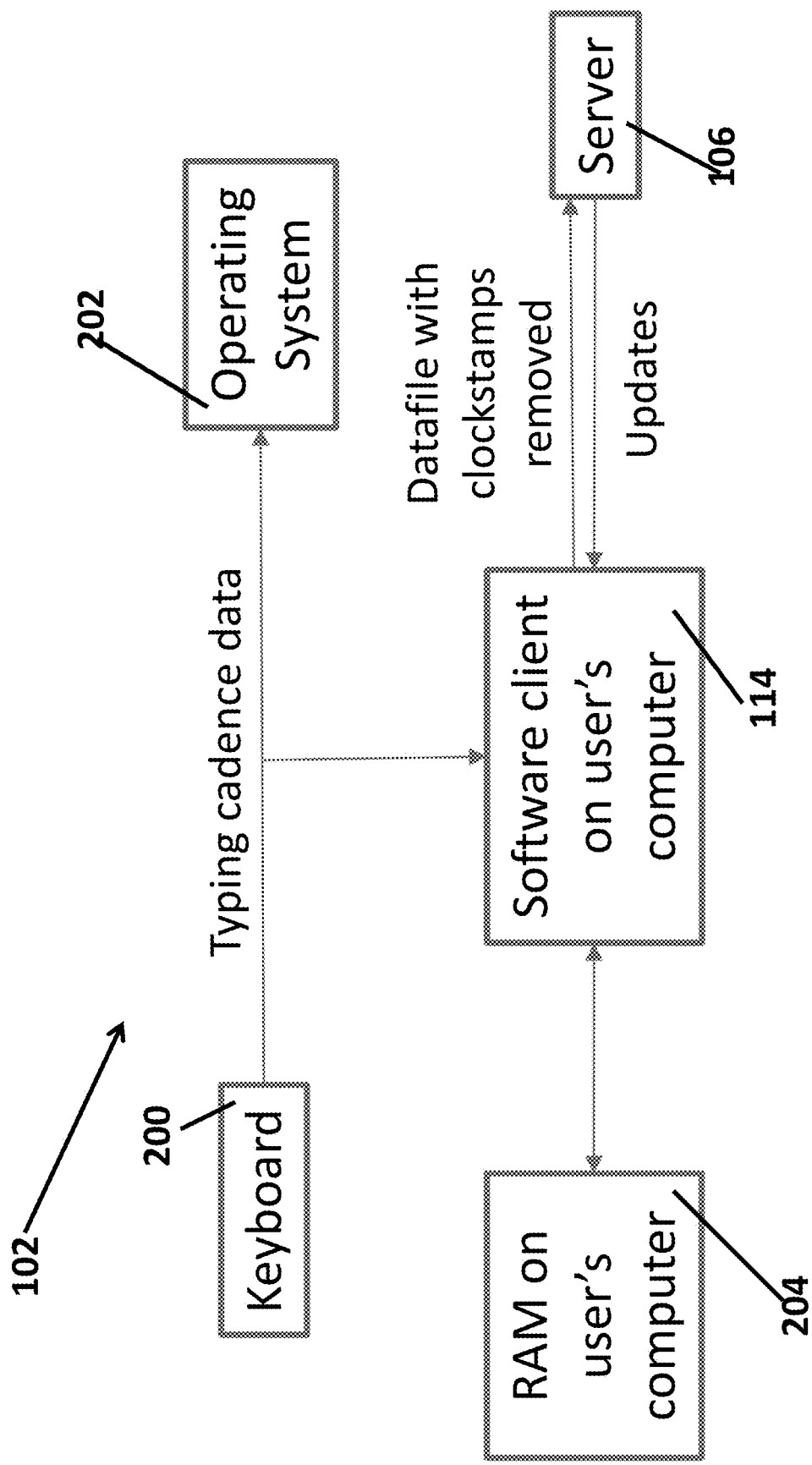
FIG. 2 illustrates an example of an implementation of a computing device that is part of the system for detecting and monitoring a neurological disorder.

FIG. 2 illustrates an example of an implementation of a computing device 102 that is part of the system for detecting and monitoring a neurological disorder. Each computing device 102 may include an input device 200, such as the keyboard as shown in FIG. 2, an operating system 202, memory 204, such as RAM in the computing device and the typing cadence component 114. The operating system 202 may include, for example, an Apple OS operating system for computers, a UNIX or UNIX like operating system, a Microsoft Windows operating system, an Apple iOS mobile operating system or the Android operating system. In operation as shown in FIG. 2, the user may user the input device to type and the typing cadence component 114 (in combination with the operating system 202) may gather data about the typing of the user as well as the typing cadence data of the user which are sent to the typing cadence component 114. The typing cadence component 114 may then store the typing cadence data for a period of time and then sent a datafile with the clockstamps removed (as described above) to the backend component 106. The typing cadence component 114 may also receive updates from the backend component 106. The updates may include, for example, how many characters the typing cadence component on each computing device will record prior to sending a data file, a particular time of day that the client should stop and send a data file, etc. Appendix B contains an example of a document that was entered by a user using an input device and Appendix A is an example of a portion of the key action data stream that is generated based on the document in Appendix B being typed by a particular user.

Figure 3:
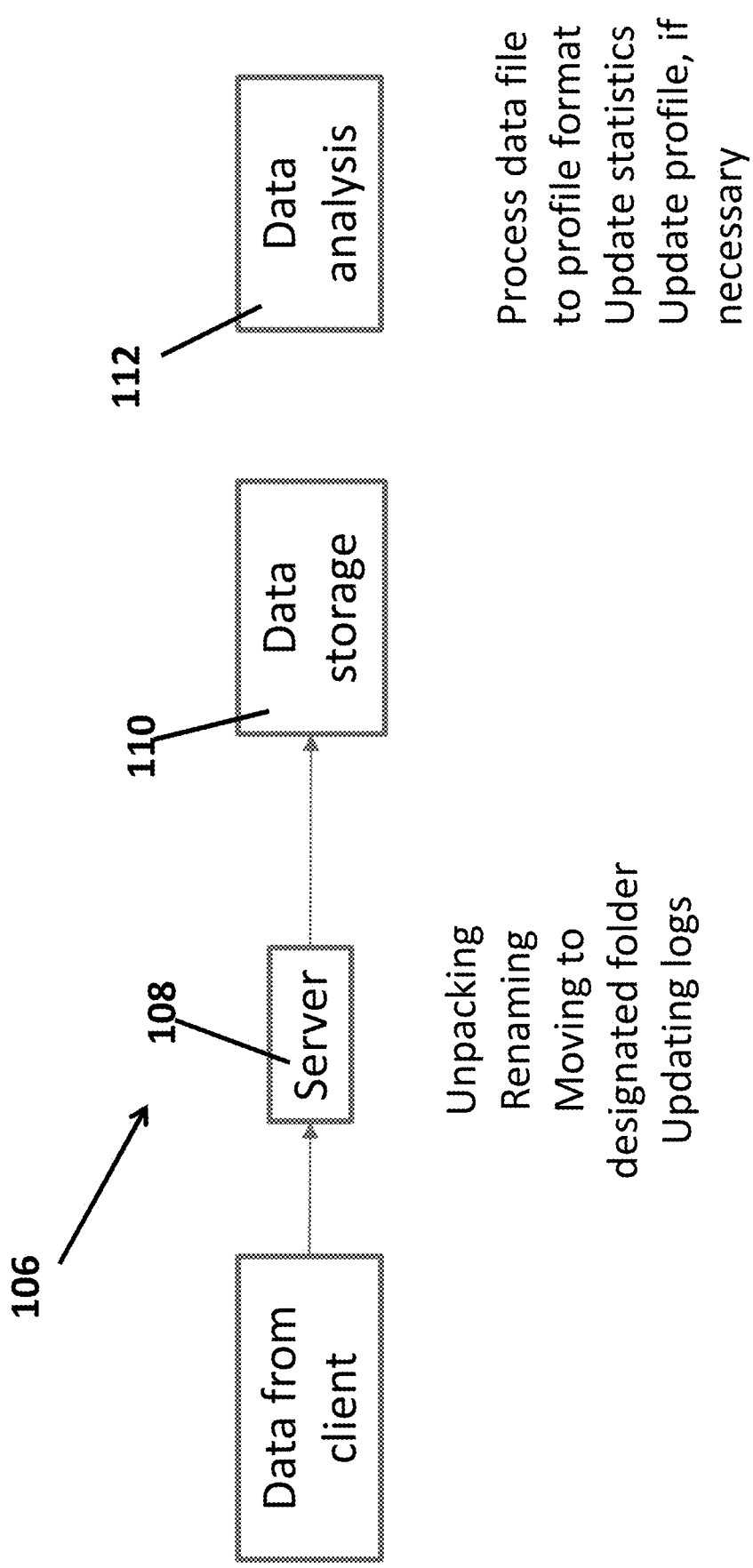
FIG. 3 illustrates an example of an implementation of a backend component that is part of the system for detecting and monitoring a neurological disorder.

FIG. 3 illustrates an example of an implementation of a backend component 106 that is part of the system for detecting and monitoring a neurological disorder. The backend component 106 may have the one or more front end components 108, one or more data stores 110 and one or more data analytics components 112 that are connected to each other as shown in FIG. 2. In this implementation of the backend component, the one or more front end components 108 may perform various actions with respect to the incoming key action data from each user. For example, the one or more front end components 108 may unpack the key action data stream, rename the key action data stream, move the key action data stream to a designated folder and update a set of log files about the key action data streams. The one or more front end components 108 may be implemented as one or more desktop computers, one or more laptop computers or one or more cloud computing resources and may execute various pieces of software/code including, for example, Windows, Perl, Java Scripts, Microsoft Office and Visual basic. The one or more data stores 110 may be used to store the various key action data streams and may segregate the key action data stream for each user into a separate storage area, such as a folder for example. The one or more data stores 110 may be implemented in a general purpose computer, specialized computer for high volume storage and complex access or a combination of hardware and software and may execute various pieces of software/code including, for example, Excel and Windows Explorer. The one or more data analytics components 112 may process each key action data file in order to convert that file into a common profile format and then update any statistics and profile about the user as described below in more detail. The one or more data analytics components 112 may be implemented using a general purpose computer and may execute various pieces of software/code including, for example, Excel, other statistical packages, such as SPSS, R and big data analytics.

Figure 4:
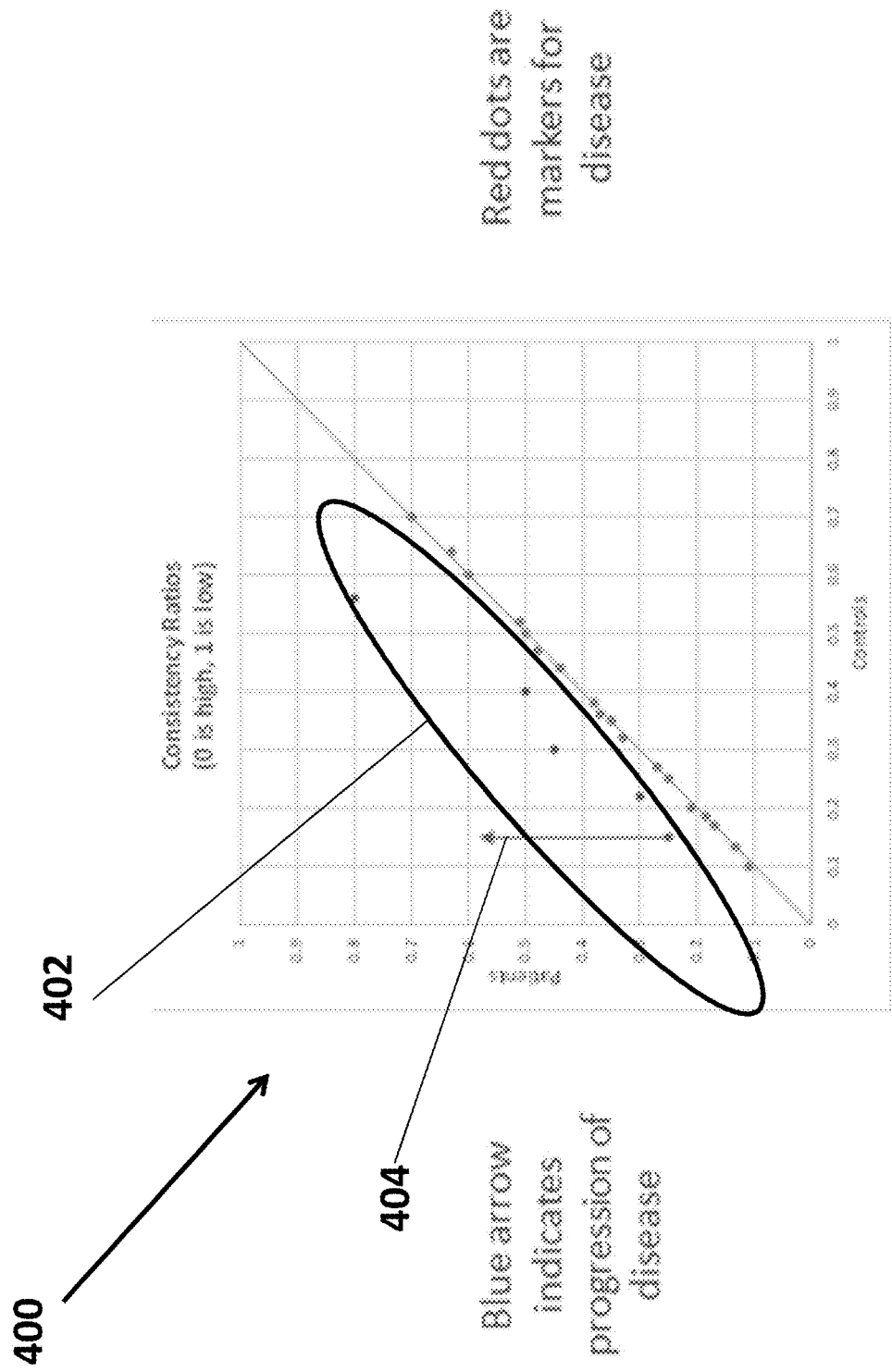
FIG. 4 illustrates an example of the data generated by the system shown in FIG. 1.

FIG. 4 illustrates an example of the data generated 400 by the system shown in FIG. 1. In particular, the graph 400 shows the consistency ratios for a set of control subjects (that do not have any neurological disorder) and a set of patients with some neurological disorder. The consistency ratios may range from 0 (high consistency ratio) to 1 (low consistency ratio.) As shown in the graph, the control subjects have data values for a key action cadence that are near the midline indicating normal cognitive function. In contrast, the patients have data points 402 above the midline that are markers for a neurological condition. In the graph in FIG. 4, the key action data (described elsewhere) may be used to calculate the inconsistency values shown in FIG. 4. For example, a coefficient of variance algorithm may be used as well as other algorithms to determine the inconsistency values. In addition, an arrow 404 superimposed on the graph and its data shows the data values changes that show a progression of the cognitive disease.

Figure 5:
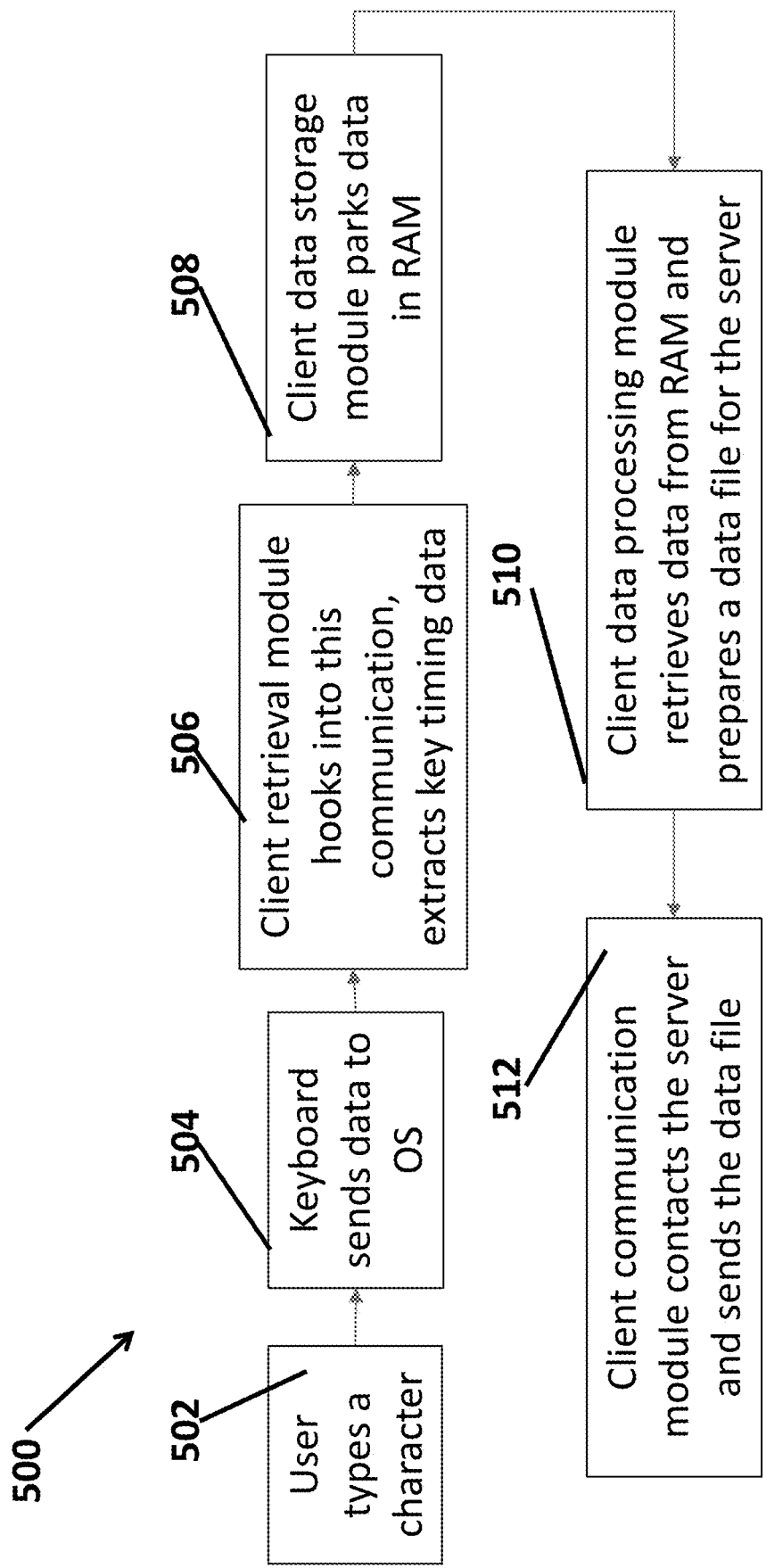
FIG. 5 illustrates an example of the processes performed by each computing device of the system for detecting and monitoring a neurological disorder.

FIG. 5 illustrates an example of the processes 500 performed by each computing device of the system for detecting and monitoring a neurological disorder. When the user types a character on the input device (502), the input device records data related to each key event/action. The key events/actions may be either a key press action (key-down) or a release of a key (key-up.) For each such event/action, the input device records the key identifier, the action being performed on the identified key and the clock time in long times, i.e. the time in milliseconds since Jan. 1, 1950. Once the key event/action data has been recorded, the key event data may be sent to the OS (operating system) (504). The typing cadence component may hook into this communication and extracts the data being sent (506) using a standard known API. The data that is extracted by the typing cadence component may be stored (508) in the computing device. In one embodiment, the data may be stored in the memory of the computing device. When the key action data stored in the computing device reaches a certain threshold (which can be set by a customer and changed remotely) or other events (such as computer shut down), the typing cadence component may trigger the sending of a data file and the typing cadence component may prepare the data file to be sent to the server (510). During the preparation of the key action data file, the typing cadence component may calculate differential times, i.e. the time a key is held down and then released (aka dwell time) and the time between key-down on one key and key-down on the next key (aka flight time) based on the extracted key action data. The key action data (and the calculated differential times) then may be sent to the backend component (512.) In some embodiments, the key action data file from each computing device may be encrypted for security so that the backend component may perform decryption on the key action data files. In one embodiment, the key action data file may have a format that may include:
 (1) Key 1 identification
 (2) Key 2 identification (if the same as Key 1, dwell time; if different, flight time; and
 (3) Time1, time2, time3, time4, etc. data points for every time a Key1-Key2 sequence occurred.

An example of the key action data file having this format is shown in more detail in Appendix A that was discussed above in more detail.

Figure 6:
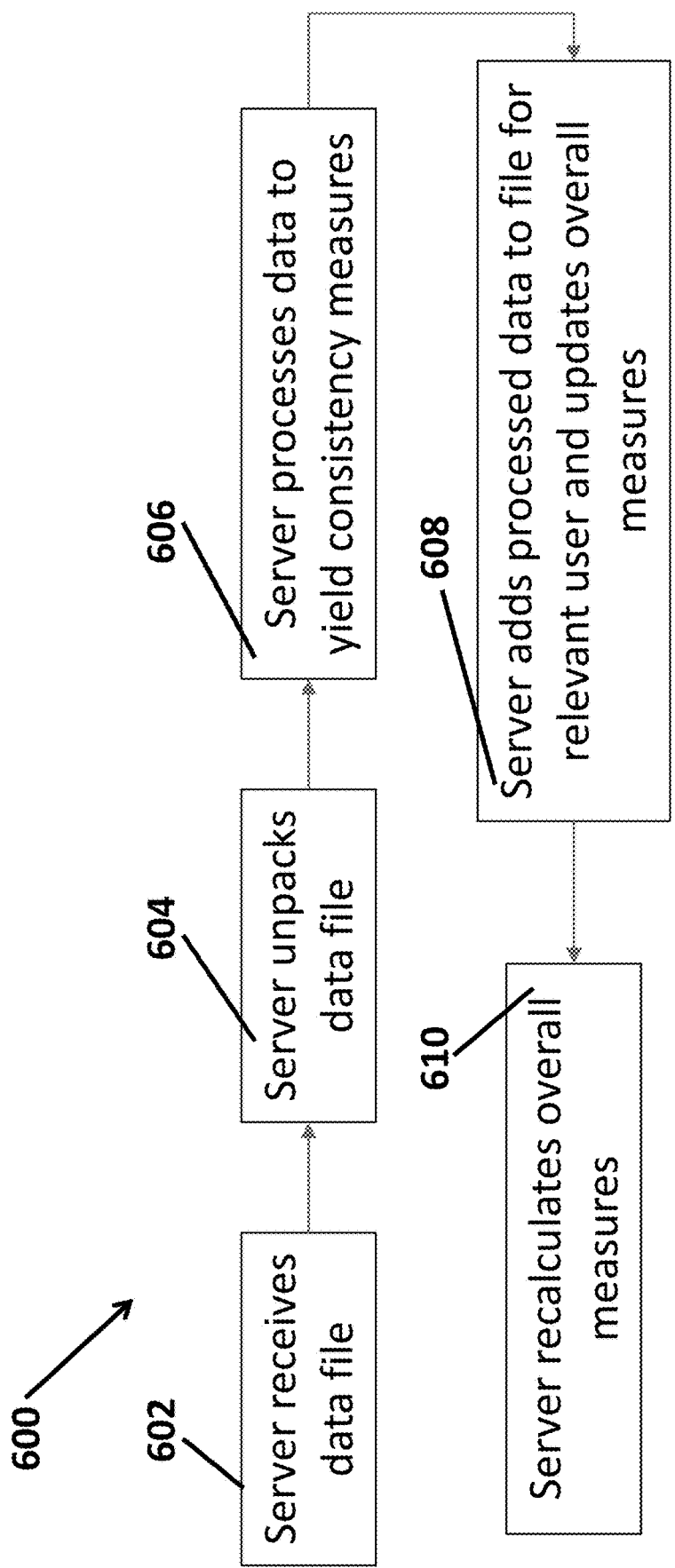
FIG. 6 illustrates an example of the processes performed by the backend component of the system for detecting and monitoring a neurological disorder.

FIG. 6 illustrates an example of the processes 600 performed by the backend component of the system for detecting and monitoring a neurological disorder. The backend component 106 may receive the key action data file (602) and may then unpack the data file, which may be in a .bin format and converts into a .csv format (spreadsheet format) to be read in Excel or other protocols (604). The backend component may process and use the key action cadence data to calculate various statistical properties, including a measure of consistency (606). The backend component may then add the processed data to a file for the relevant user and update overall measures (608). The overall measures may be, for example, weighted averages determined based on the measure of inconsistency values. The backend component may then recalculate the overall measures (610) which are used to detect and then monitor a neurological disorder as shown in FIG. 4.

While the foregoing has been with reference to a particular embodiment of the invention, it will be appreciated by those skilled in the art that changes in this embodiment may be made without departing from the principles and spirit of the disclosure, the scope of which is defined by the appended claims.

APPENDIX A

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 8 | 8 | 104 | 80 | 104 | 104 | 120 | 176 | 120 | 104 | 144 | 72 |
| 32 | 8 | 5632 | 10079 | | | | | | | | |
| 69 | 8 | 1560 | | | | | | | | | |
| 79 | 8 | 3368 | 9471 | | | | | | | | |
| 83 | 8 | 5232 | 3279 | | | | | | | | |
| 84 | 8 | 1288 | | | | | | | | | |
| 87 | 8 | 2320 | | | | | | | | | |
| 89 | 8 | 2296 | | | | | | | | | |
| 187 | 8 | 1448 | | | | | | | | | |
| 13 | 13 | 112 | 88 | 80 | 128 | 88 | 120 | 97 | 112 | 96 | 144 |
| 32 | 13 | 5943 | | | | | | | | | |
| 78 | 13 | 4408 | | | | | | | | | |
| 83 | 13 | 3416 | | | | | | | | | |
| 190 | 13 | 1960 | 936 | 1280 | 22431 | 4415 | 17024 | | | | |
| 191 | 13 | 15288 | | | | | | | | | |
| 32 | 32 | 96 | 96 | 88 | 80 | 96 | 96 | 96 | 88 | 71 | 72 |
| 54 | 32 | 1280 | | | | | | | | | |
| 65 | 32 | 2327 | 168 | 160 | 160 | 232 | 145 | 192 | | | |
| 66 | 32 | 216 | | | | | | | | | |
| 67 | 32 | 2568 | 6007 | | | | | | | | |
| 68 | 32 | 488 | 240 | 3176 | 144 | 144 | 3008 | 88 | 3645 | 1232 | 112 |
| 69 | 32 | 160 | 328 | 240 | 224 | 216 | 1400 | 1528 | 712 | 152 | 176 |
| 70 | 32 | 936 | 168 | 160 | 160 | 176 | 144 | 1312 | 152 | 216 | 136 |
| 71 | 32 | 416 | 240 | 257 | 936 | 3328 | 368 | 1536 | 2328 | 10943 | 296 |
| 72 | 32 | 256 | 224 | 264 | 296 | 1104 | 1488 | | | | |
| 75 | 32 | 1776 | 2335 | 1552 | | | | | | | |
| 76 | 32 | 2431 | 3424 | 1128 | 400 | 2488 | 488 | 1160 | 1303 | | |
| 77 | 32 | 280 | 1344 | 2616 | | | | | | | |
| 78 | 32 | 192 | 192 | 1767 | 215 | 216 | 496 | 248 | 216 | 296 | 416 |
| 79 | 32 | 272 | 321 | 320 | 264 | 312 | 288 | 928 | 5192 | 288 | 256 |
| 80 | 32 | 4816 | 496 | | | | | | | | |
| 82 | 32 | 1096 | 135 | 120 | 304 | 424 | 208 | 4943 | 184 | 126 | 232 |
| 83 | 32 | 312 | 192 | 2544 | 2440 | 1320 | 3976 | 2160 | 192 | 2344 | 1600 |
| 84 | 32 | 360 | 296 | 1296 | 464 | 416 | 280 | 296 | 280 | 304 | 264 |
| 85 | 32 | 248 | | | | | | | | | |
| 87 | 32 | 1640 | 192 | 2376 | 7895 | 400 | | | | | |
| 89 | 32 | 4264 | 856 | 720 | 2791 | 2343 | 256 | 280 | 280 | 1632 | 352 |
| 186 | 32 | 608 | 480 | | | | | | | | |
| 188 | 32 | 256 | 272 | 256 | 192 | 264 | 240 | 208 | 208 | 256 | 240 |
| 189 | 32 | 976 | 976 | | | | | | | | |
| 190 | 32 | 1440 | 256 | 256 | 264 | 1472 | 240 | 408 | 568 | 264 | 272 |
| 37 | 37 | 104 | 80 | 96 | 128 | 104 | 136 | | | | |
| 77 | 37 | 1856 | | | | | | | | | |
| 48 | 48 | 96 | 120 | | | | | | | | |
| 57 | 48 | 1160 | | | | | | | | | |
| 186 | 48 | 328 | | | | | | | | | |
| 32 | 49 | 2799 | | | | | | | | | |
| 49 | 49 | 191 | 129 | 120 | | | | | | | |
| 186 | 49 | 1695 | | | | | | | | | |
| 32 | 50 | 592 | 824 | | | | | | | | |
| 48 | 50 | 424 | | | | | | | | | |
| 50 | 50 | 88 | 120 | 96 | | | | | | | |
| 49 | 54 | 273 | | | | | | | | | |
| 50 | 54 | 320 | | | | | | | | | |
| 54 | 54 | 96 | 96 | | | | | | | | |
| 49 | 57 | 592 | | | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 57 | 57 | 73 | 119 | | | | | | | | |
| 32 | 65 | 7615 | 200 | 584 | 840 | 216 | 832 | 896 | 208 | 208 | 2135 |
| 65 | 65 | 88 | 128 | 119 | 120 | 184 | 136 | 168 | 96 | 136 | 168 |
| 66 | 65 | 216 | | | | | | | | | |
| 67 | 65 | 216 | 216 | 512 | 392 | 608 | 416 | 464 | 431 | | |
| 68 | 65 | 408 | 344 | | | | | | | | |
| 69 | 65 | 216 | 288 | 368 | 328 | 616 | 296 | 352 | 424 | 344 | 336 |
| 70 | 65 | 232 | 288 | | | | | | | | |
| 71 | 65 | 368 | 359 | | | | | | | | |
| 72 | 65 | 424 | 288 | 480 | 304 | 584 | 424 | 240 | 168 | 400 | 368 |
| 73 | 65 | 488 | | | | | | | | | |
| 75 | 65 | 256 | | | | | | | | | |
| 76 | 65 | 160 | 601 | 631 | 288 | 513 | | | | | |
| 77 | 65 | 368 | 423 | 216 | 976 | 352 | 256 | 464 | 336 | 392 | |
| 78 | 65 | 464 | 464 | | | | | | | | |
| 79 | 65 | 936 | | | | | | | | | |
| 80 | 65 | 632 | 464 | 432 | | | | | | | |
| 82 | 65 | 216 | 856 | 560 | 600 | 344 | 360 | 792 | | | |
| 84 | 65 | 248 | 296 | 288 | | | | | | | |
| 86 | 65 | 424 | 416 | 416 | 400 | 568 | | | | | |
| 87 | 65 | 280 | 320 | 432 | 360 | 256 | | | | | |
| 32 | 66 | 976 | 264 | 215 | 312 | 256 | 1112 | 264 | 208 | 1184 | 264 |
| 65 | 66 | 160 | 192 | | | | | | | | |
| 66 | 66 | 120 | 80 | 72 | 80 | 96 | 72 | 64 | 96 | 88 | 96 |
| 69 | 66 | 704 | | | | | | | | | |
| 73 | 66 | 280 | | | | | | | | | |
| 79 | 66 | 352 | | | | | | | | | |
| 85 | 66 | 288 | | | | | | | | | |
| 160 | 66 | 192 | 168 | 159 | | | | | | | |
| 32 | 67 | 240 | 1568 | 240 | 288 | 351 | 424 | 472 | 4816 | 840 | 496 |
| 65 | 67 | 216 | 192 | 448 | | | | | | | |
| 67 | 67 | 72 | 120 | 144 | 144 | 96 | 96 | 72 | 104 | 137 | 160 |
| 69 | 67 | 304 | 304 | 328 | | | | | | | |
| 73 | 67 | 216 | 392 | 265 | 327 | 352 | | | | | |
| 78 | 67 | 248 | 232 | 216 | 216 | 232 | | | | | |
| 82 | 67 | 304 | 216 | | | | | | | | |
| 83 | 67 | 2304 | 352 | 272 | 288 | 280 | 312 | | | | |
| 85 | 67 | 288 | 304 | 256 | 256 | 256 | | | | | |
| 160 | 67 | 352 | 208 | | | | | | | | |
| 189 | 67 | 376 | | | | | | | | | |
| 32 | 68 | 1191 | 1344 | 376 | 68029 | 1096 | | | | | |
| 65 | 68 | 136 | 344 | | | | | | | | |
| 68 | 68 | 120 | 96 | 104 | 88 | 120 | 112 | 120 | 120 | 88 | 96 |
| 69 | 68 | 336 | 256 | 322 | 328 | 272 | 312 | 320 | 280 | | |
| 73 | 68 | 384 | 256 | 240 | 256 | 168 | | | | | |
| 76 | 68 | 200 | 424 | | | | | | | | |
| 78 | 68 | 360 | 232 | 272 | 256 | 232 | 264 | 256 | 280 | 280 | 280 |
| 79 | 68 | 304 | 392 | 336 | 304 | 352 | | | | | |
| 82 | 68 | 232 | 240 | 288 | | | | | | | |
| 32 | 69 | 232 | 1888 | 496 | 281 | 864 | 216 | 368 | 488 | 232 | 424 |
| 66 | 69 | 240 | 232 | 264 | 359 | 232 | 328 | 280 | 240 | 232 | |
| 67 | 69 | 304 | 368 | 272 | 448 | 304 | 352 | 407 | 456 | 312 | |
| 68 | 69 | 240 | 240 | 256 | 216 | 200 | 192 | 232 | 240 | 231 | 216 |
| 69 | 69 | 96 | 160 | 96 | 104 | 80 | 120 | 144 | 144 | 168 | 80 |
| 70 | 69 | 392 | 520 | | | | | | | | |
| 71 | 69 | 280 | 312 | 368 | 752 | | | | | | |
| 72 | 69 | 304 | 312 | 320 | 384 | 392 | 856 | 384 | 272 | 208 | 424 |
| 73 | 69 | 496 | 279 | 2240 | 232 | 184 | 408 | 288 | 248 | 246 | 264 |
| 75 | 69 | 344 | 216 | 400 | 192 | 240 | 216 | 288 | | | |
| 76 | 69 | 344 | 656 | 256 | 344 | 904 | 232 | | | | |
| 77 | 69 | 440 | 256 | 264 | 256 | 240 | 184 | 848 | 216 | 368 | 1520 |
| 78 | 69 | 256 | 560 | 416 | 160 | 336 | 416 | 424 | 336 | 344 | 328 |
| 80 | 69 | 248 | 216 | 208 | 280 | 432 | | | | | |
| 82 | 69 | 239 | 224 | 240 | 256 | 224 | 312 | 216 | 232 | 215 | 191 |
| 83 | 69 | 208 | 240 | 280 | 256 | 232 | 264 | 264 | 289 | 256 | 240 |
| 84 | 69 | 192 | 384 | 280 | 328 | 264 | 232 | 264 | | | |
| 86 | 69 | 160 | 280 | 200 | 208 | 240 | 184 | 232 | 376 | 288 | 272 |
| 87 | 69 | 200 | 352 | 264 | 232 | 241 | 399 | | | | |
| 89 | 69 | 368 | 240 | 288 | 376 | 345 | | | | | |
| 160 | 69 | 232 | 216 | | | | | | | | |
| 32 | 70 | 384 | 1760 | 233 | 2064 | 400 | 1456 | 360 | 1816 | 232 | 352 |
| 65 | 70 | 240 | | | | | | | | | |
| 68 | 70 | 288 | | | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 69 | 70 | 432 | 1680 | | | | | | | | |
| 70 | 70 | 96 | 64 | 136 | 112 | 88 | 96 | 88 | 95 | 112 | 96 |
| 73 | 70 | 344 | 272 | | | | | | | | |
| 79 | 70 | 336 | 304 | 424 | 304 | 288 | 256 | 328 | 328 | 376 | 368 |
| 160 | 70 | 256 | 216 | | | | | | | | |
| 32 | 71 | 312 | 592 | 305 | 328 | 351 | | | | | |
| 65 | 71 | 192 | 192 | | | | | | | | |
| 71 | 71 | 88 | 88 | 88 | 72 | 96 | 96 | 96 | 80 | 88 | 112 |
| 73 | 71 | 400 | 304 | 360 | 312 | 376 | | | | | |
| 78 | 71 | 280 | 336 | 264 | 272 | 304 | 312 | 255 | 360 | 384 | 312 |
| 79 | 71 | 384 | | | | | | | | | |
| 32 | 72 | 304 | 1016 | 976 | 5680 | 328 | 360 | 680 | 1472 | 304 | 280 |
| 67 | 72 | 192 | 192 | 312 | 344 | 448 | 551 | 256 | 232 | 208 | 168 |
| 71 | 72 | 240 | | | | | | | | | |
| 72 | 72 | 96 | 104 | 88 | 96 | 112 | 64 | 96 | 120 | 72 | 80 |
| 83 | 72 | 168 | 192 | 216 | | | | | | | |
| 84 | 72 | 264 | 248 | 288 | 216 | 160 | 184 | 200 | 304 | 192 | 272 |
| 87 | 72 | 256 | 607 | 384 | 200 | | | | | | |
| 8 | 73 | 2815 | 408 | | | | | | | | |
| 32 | 73 | 464 | 312 | 304 | 1112 | 504 | 296 | 376 | 360 | 3136 | 312 |
| 65 | 73 | 312 | | | | | | | | | |
| 66 | 73 | 744 | 296 | | | | | | | | |
| 67 | 73 | 264 | 264 | 208 | 224 | 280 | | | | | |
| 68 | 73 | 303 | 392 | 264 | 280 | 240 | | | | | |
| 69 | 73 | 264 | 208 | 344 | | | | | | | |
| 70 | 73 | 400 | 176 | 248 | 256 | 320 | | | | | |
| 71 | 73 | 472 | 552 | 4792 | | | | | | | |
| 72 | 73 | 544 | 432 | 488 | 608 | | | | | | |
| 73 | 73 | 88 | 88 | 72 | 72 | 80 | 72 | 88 | 96 | 88 | 64 |
| 75 | 73 | 232 | 304 | 248 | | | | | | | |
| 76 | 73 | 312 | 296 | 240 | 328 | 312 | 296 | 584 | | | |
| 78 | 73 | 296 | 368 | 519 | | | | | | | |
| 79 | 73 | 216 | | | | | | | | | |
| 80 | 73 | 288 | 247 | 311 | | | | | | | |
| 82 | 73 | 216 | 432 | 240 | 728 | 376 | 240 | 240 | 256 | 200 | 304 |
| 83 | 73 | 408 | 312 | 497 | 304 | 217 | 305 | 216 | 344 | | |
| 84 | 73 | 528 | 560 | 544 | 552 | 496 | 264 | 536 | 312 | 136 | 632 |
| 85 | 73 | 536 | 417 | 232 | | | | | | | |
| 86 | 73 | 512 | | | | | | | | | |
| 87 | 73 | 672 | 639 | 288 | 271 | | | | | | |
| 160 | 73 | 544 | 352 | 328 | 256 | 344 | 304 | | | | |
| 74 | 74 | 88 | | | | | | | | | |
| 160 | 74 | 208 | | | | | | | | | |
| 32 | 75 | 1120 | 1992 | | | | | | | | |
| 65 | 75 | 248 | 184 | 384 | 352 | 280 | 240 | | | | |
| 67 | 75 | 264 | 424 | 327 | | | | | | | |
| 69 | 75 | 281 | | | | | | | | | |
| 75 | 75 | 95 | 112 | 80 | 72 | 72 | 104 | 96 | 88 | 96 | 88 |
| 78 | 75 | 472 | | | | | | | | | |
| 82 | 75 | 240 | | | | | | | | | |
| 83 | 75 | 256 | 280 | 230 | 184 | 265 | | | | | |
| 32 | 76 | 320 | 512 | 584 | 752 | 544 | 600 | 2608 | | | |
| 65 | 76 | 536 | 448 | 264 | 303 | 232 | 408 | | | | |
| 66 | 76 | 512 | 616 | 728 | 400 | | | | | | |
| 69 | 76 | 352 | 328 | 344 | 360 | 232 | 625 | 904 | | | |
| 71 | 76 | 648 | | | | | | | | | |
| 73 | 76 | 360 | 304 | 280 | 486 | 344 | 280 | | | | |
| 75 | 76 | 192 | | | | | | | | | |
| 76 | 76 | 96 | 96 | 96 | 96 | 96 | 104 | 72 | 96 | 96 | 104 |
| 78 | 76 | 488 | | | | | | | | | |
| 79 | 76 | 240 | 216 | 256 | 240 | | | | | | |
| 80 | 76 | 224 | 247 | | | | | | | | |
| 82 | 76 | 152 | 600 | 608 | | | | | | | |
| 83 | 76 | 240 | | | | | | | | | |
| 84 | 76 | 680 | | | | | | | | | |
| 85 | 76 | 903 | 560 | 440 | 528 | | | | | | |
| 32 | 77 | 256 | 344 | 2376 | 304 | 1360 | 232 | 560 | 1696 | 984 | 1480 |
| 65 | 77 | 264 | 288 | 216 | 304 | | | | | | |
| 69 | 77 | 952 | 376 | 264 | 464 | | | | | | |
| 73 | 77 | 296 | | | | | | | | | |
| 77 | 77 | 112 | 120 | 136 | 112 | 71 | 96 | 104 | 88 | 48 | 72 |
| 78 | 77 | 1352 | | | | | | | | | |
| 79 | 77 | 400 | 280 | 288 | 312 | 304 | 280 | 328 | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 80 | 77 | 880 | 496 | | | | | | | | |
| 84 | 77 | 1912 | 464 | 472 | 760 | | | | | | |
| 85 | 77 | 320 | | | | | | | | | |
| 160 | 77 | 608 | 192 | 232 | 376 | | | | | | |
| 8 | 78 | 2592 | | | | | | | | | |
| 32 | 78 | 232 | 248 | 1536 | 256 | 911 | 296 | 904 | 6047 | 1344 | 2440 |
| 65 | 78 | 208 | 280 | 568 | 184 | 264 | 264 | 224 | 296 | 144 | 264 |
| 69 | 78 | 176 | 313 | 352 | 408 | 208 | 256 | 144 | 256 | 184 | 184 |
| 71 | 78 | 280 | | | | | | | | | |
| 72 | 78 | 264 | | | | | | | | | |
| 73 | 78 | 280 | 296 | 328 | 344 | 304 | 288 | 288 | 304 | 248 | 272 |
| 75 | 78 | 5880 | | | | | | | | | |
| 78 | 78 | 96 | 96 | 96 | 72 | 96 | 88 | 96 | 64 | 64 | 48 |
| 79 | 78 | 400 | 296 | 320 | 288 | 304 | 328 | 328 | 328 | 336 | 328 |
| 82 | 78 | 96 | 256 | 304 | | | | | | | |
| 83 | 78 | 152 | | | | | | | | | |
| 85 | 78 | 367 | 249 | 288 | 304 | 240 | 256 | 264 | 280 | 304 | 344 |
| 87 | 78 | 1072 | 240 | | | | | | | | |
| 8 | 79 | 496 | | | | | | | | | |
| 32 | 79 | 552 | 1840 | 408 | 2599 | 680 | 424 | 368 | 752 | 8295 | 352 |
| 67 | 79 | 216 | 512 | 272 | 464 | 256 | 368 | 296 | 280 | 216 | 256 |
| 68 | 79 | 512 | | | | | | | | | |
| 69 | 79 | 4408 | | | | | | | | | |
| 70 | 79 | 535 | 280 | 264 | 568 | 272 | 264 | 280 | | | |
| 71 | 79 | 624 | 432 | | | | | | | | |
| 72 | 79 | 424 | 656 | 488 | 530 | 496 | 472 | 360 | | | |
| 73 | 79 | 216 | 208 | 232 | 216 | 216 | 200 | 216 | 216 | 231 | 240 |
| 76 | 79 | 264 | 296 | 256 | 328 | 224 | 288 | 216 | | | |
| 77 | 79 | 312 | 536 | 416 | 568 | 336 | 344 | | | | |
| 78 | 79 | 432 | 648 | 376 | 352 | 296 | 328 | 528 | 552 | 760 | 560 |
| 79 | 79 | 96 | 88 | 96 | 72 | 81 | 96 | 88 | 96 | 96 | 128 |
| 80 | 79 | 240 | 240 | 1128 | 240 | 288 | 392 | | | | |
| 82 | 79 | 280 | 424 | 288 | 192 | 240 | 256 | 208 | 256 | 343 | 328 |
| 83 | 79 | 208 | 384 | 336 | 528 | 312 | 280 | 248 | 544 | | |
| 84 | 79 | 304 | 1071 | 440 | 712 | 256 | 536 | 560 | 344 | 208 | 264 |
| 86 | 79 | 400 | 376 | 656 | | | | | | | |
| 87 | 79 | 760 | | | | | | | | | |
| 89 | 79 | 192 | 256 | 240 | | | | | | | |
| 32 | 80 | 872 | 408 | 336 | 512 | 608 | 440 | 728 | 584 | 984 | 945 |
| 50 | 80 | 1384 | | | | | | | | | |
| 54 | 80 | 2175 | | | | | | | | | |
| 65 | 80 | 424 | 312 | | | | | | | | |
| 69 | 80 | 424 | 328 | | | | | | | | |
| 77 | 80 | 312 | 512 | 576 | | | | | | | |
| 78 | 80 | 632 | | | | | | | | | |
| 79 | 80 | 232 | 1096 | 680 | | | | | | | |
| 80 | 80 | 88 | 72 | 104 | 80 | 104 | 72 | 95 | 96 | 120 | 104 |
| 82 | 80 | 216 | 208 | | | | | | | | |
| 83 | 80 | 984 | 256 | 232 | 425 | 304 | | | | | |
| 85 | 80 | 488 | 512 | 576 | | | | | | | |
| 88 | 80 | 216 | | | | | | | | | |
| 89 | 80 | 264 | | | | | | | | | |
| 32 | 81 | 439 | 448 | | | | | | | | |
| 81 | 81 | 104 | 120 | | | | | | | | |
| 32 | 82 | 856 | 152 | 168 | 136 | 208 | 4032 | 176 | 192 | 704 | 216 |
| 65 | 82 | 407 | 192 | 256 | 160 | 240 | 191 | 184 | 200 | 152 | 192 |
| 66 | 82 | 408 | | | | | | | | | |
| 67 | 82 | 337 | | | | | | | | | |
| 68 | 82 | 1264 | | | | | | | | | |
| 69 | 82 | 24 | 240 | 280 | 176 | 112 | 248 | 152 | 264 | 168 | 240 |
| 70 | 82 | 472 | 464 | | | | | | | | |
| 71 | 82 | 280 | 305 | | | | | | | | |
| 73 | 82 | 280 | 200 | | | | | | | | |
| 79 | 82 | 240 | 656 | 249 | 360 | 264 | 672 | 352 | 240 | 329 | 312 |
| 80 | 82 | 416 | 280 | 360 | 328 | 280 | 336 | 352 | | | |
| 82 | 82 | 136 | 144 | 104 | 72 | 120 | 144 | 72 | 120 | 120 | 96 |
| 84 | 82 | 232 | 216 | | | | | | | | |
| 85 | 82 | 304 | 328 | 416 | 280 | 232 | 256 | 391 | 232 | 424 | |
| 189 | 82 | 304 | | | | | | | | | |
| 8 | 83 | 336 | 1184 | | | | | | | | |
| 32 | 83 | 192 | 360 | 232 | 888 | 424 | 256 | 184 | 1120 | 232 | 192 |
| 48 | 83 | 4088 | | | | | | | | | |
| 65 | 83 | 280 | 240 | 384 | 328 | 296 | 280 | 264 | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 66 | 83 | 288 | | | | | | | | | |
| 69 | 83 | 344 | 256 | 328 | 280 | 240 | 312 | 304 | 288 | 336 | 312 |
| 73 | 83 | 303 | 368 | 456 | 423 | 610 | 304 | 472 | 224 | 312 | 400 |
| 78 | 83 | 560 | 1992 | 424 | 336 | 360 | 1647 | 279 | 264 | | |
| 79 | 83 | 254 | | | | | | | | | |
| 80 | 83 | 520 | | | | | | | | | |
| 82 | 83 | 400 | 352 | 176 | 183 | 192 | 216 | 256 | 1208 | 27558 | |
| 83 | 83 | 96 | 88 | 96 | 96 | 88 | 136 | 112 | 112 | 112 | 135 |
| 84 | 83 | 696 | 208 | 192 | 232 | 280 | 464 | 616 | | | |
| 85 | 83 | 448 | 360 | 232 | 320 | | | | | | |
| 89 | 83 | 256 | | | | | | | | | |
| 160 | 83 | 960 | 544 | | | | | | | | |
| 222 | 83 | 264 | 496 | 392 | | | | | | | |
| 32 | 84 | 1016 | 2160 | 1608 | 368 | 1032 | 376 | 232 | 1520 | 1360 | 2680 |
| 65 | 84 | 280 | 288 | 296 | 216 | 160 | 264 | 224 | 192 | 328 | 240 |
| 67 | 84 | 488 | 320 | | | | | | | | |
| 69 | 84 | 232 | 184 | 144 | 336 | 272 | 160 | 168 | 3696 | | |
| 72 | 84 | 288 | | | | | | | | | |
| 73 | 84 | 368 | 392 | 1624 | 744 | 1880 | 360 | 360 | 303 | 376 | 264 |
| 76 | 84 | 376 | | | | | | | | | |
| 78 | 84 | 352 | 432 | 288 | 384 | 512 | 400 | 312 | 320 | 184 | 256 |
| 79 | 84 | 544 | 232 | 288 | 1216 | 2880 | | | | | |
| 80 | 84 | 472 | 440 | | | | | | | | |
| 82 | 84 | 112 | | | | | | | | | |
| 83 | 84 | 232 | 88 | 224 | 168 | 120 | 112 | 184 | 120 | 216 | 128 |
| 84 | 84 | 88 | 112 | 88 | 104 | 88 | 96 | 160 | 112 | 80 | 88 |
| 85 | 84 | 320 | 264 | 296 | 336 | 376 | 376 | 232 | 328 | 272 | |
| 88 | 84 | 240 | | | | | | | | | |
| 160 | 84 | 280 | 1144 | 471 | 126 | 304 | 232 | 207 | 352 | 120 | 280 |
| 222 | 84 | 376 | | | | | | | | | |
| 32 | 85 | 472 | 288 | 352 | 360 | 424 | 328 | 1312 | 984 | | |
| 65 | 85 | 296 | 280 | | | | | | | | |
| 66 | 85 | 376 | 432 | 520 | 464 | | | | | | |
| 68 | 85 | 497 | 216 | 256 | 232 | | | | | | |
| 69 | 85 | 600 | | | | | | | | | |
| 70 | 85 | 287 | 264 | 224 | 312 | 240 | 176 | | | | |
| 71 | 85 | 520 | | | | | | | | | |
| 74 | 85 | 257 | | | | | | | | | |
| 77 | 85 | 328 | 568 | | | | | | | | |
| 79 | 85 | 264 | 264 | 304 | 344 | 288 | 359 | 265 | 464 | 288 | 288 |
| 80 | 85 | 1632 | 4200 | 416 | | | | | | | |
| 81 | 85 | 368 | 328 | | | | | | | | |
| 82 | 85 | 568 | 320 | | | | | | | | |
| 83 | 85 | 264 | 208 | 304 | | | | | | | |
| 84 | 85 | 320 | 280 | 544 | | | | | | | |
| 85 | 85 | 63 | 96 | 96 | 96 | 73 | 120 | 88 | 120 | 80 | 120 |
| 32 | 86 | 7847 | | | | | | | | | |
| 65 | 86 | 232 | 208 | 216 | 257 | | | | | | |
| 69 | 86 | 144 | 264 | | | | | | | | |
| 73 | 86 | 304 | 416 | 360 | 328 | 360 | 351 | | | | |
| 76 | 86 | 376 | 384 | 424 | | | | | | | |
| 78 | 86 | 288 | 288 | 328 | 352 | 288 | 352 | 296 | 352 | 328 | 344 |
| 79 | 86 | 544 | 392 | 392 | 416 | 400 | 368 | 368 | | | |
| 86 | 86 | 96 | 88 | 96 | 96 | 112 | 112 | 72 | 112 | 88 | 64 |
| 8 | 87 | 1968 | | | | | | | | | |
| 32 | 87 | 264 | 224 | 888 | 912 | 240 | 184 | 1024 | 368 | 1200 | |
| 69 | 87 | 488 | 520 | 496 | 520 | 512 | 272 | | | | |
| 79 | 87 | 400 | 400 | 304 | 760 | 392 | 473 | | | | |
| 82 | 87 | 320 | | | | | | | | | |
| 84 | 87 | 728 | | | | | | | | | |
| 87 | 87 | 96 | 64 | 88 | 72 | 72 | 95 | 80 | 120 | 136 | 144 |
| 160 | 87 | 208 | 240 | 512 | 208 | 209 | | | | | |
| 69 | 88 | 304 | 304 | | | | | | | | |
| 88 | 88 | 144 | 144 | | | | | | | | |
| 32 | 89 | 2264 | 840 | 3048 | 417 | 640 | 279 | | | | |
| 65 | 89 | 264 | 232 | 288 | 352 | 463 | | | | | |
| 69 | 89 | 496 | 288 | | | | | | | | |
| 71 | 89 | 280 | | | | | | | | | |
| 75 | 89 | 336 | 495 | | | | | | | | |
| 76 | 89 | 448 | 480 | 416 | 656 | 464 | 688 | 616 | 392 | 479 | |
| 78 | 89 | 416 | 312 | | | | | | | | |
| 82 | 89 | 512 | | | | | | | | | |
| 84 | 89 | 184 | 168 | 232 | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 85 | 89 | 320 | | | | | | | | | |
| 89 | 89 | 96 | 112 | 112 | 96 | 96 | 88 | 48 | 72 | 95 | 112 |
| 160 | 89 | 208 | 647 | | | | | | | | |
| 8 | 160 | 1096 | 248 | 312 | | | | | | | |
| 13 | 160 | 2192 | 57557 | 7586 | 1887 | 2136 | 18415 | 6183 | 68748 | 18455 | 2095 |
| 32 | 160 | 240 | 864 | 3096 | 200 | 328 | 1192 | 208 | 448 | 288 | 632 |
| 37 | 160 | 7224 | | | | | | | | | |
| 49 | 160 | 919 | | | | | | | | | |
| 50 | 160 | 1120 | | | | | | | | | |
| 84 | 160 | 3760 | | | | | | | | | |
| 89 | 160 | 1048 | 4512 | | | | | | | | |
| 160 | 160 | 376 | 392 | 424 | 368 | 384 | 304 | 360 | 288 | 480 | 288 |
| 160 | 186 | 232 | 320 | 1080 | 208 | | | | | | |
| 186 | 186 | 88 | 104 | 80 | 96 | | | | | | |
| 84 | 187 | 840 | | | | | | | | | |
| 187 | 187 | 152 | | | | | | | | | |
| 65 | 188 | 4112 | | | | | | | | | |
| 69 | 188 | 4567 | | | | | | | | | |
| 71 | 188 | 4496 | | | | | | | | | |
| 72 | 188 | 4720 | | | | | | | | | |
| 78 | 188 | 2888 | | | | | | | | | |
| 82 | 188 | 4272 | | | | | | | | | |
| 83 | 188 | 3016 | 648 | 2528 | 6096 | | | | | | |
| 89 | 188 | 4760 | | | | | | | | | |
| 188 | 188 | 72 | 80 | 72 | 72 | 72 | 32 | 72 | 72 | 64 | 80 |
| 32 | 189 | 497 | 1416 | | | | | | | | |
| 69 | 189 | 1072 | | | | | | | | | |
| 87 | 189 | 560 | | | | | | | | | |
| 189 | 189 | 88 | 96 | 95 | 88 | | | | | | |
| 8 | 190 | 777 | | | | | | | | | |
| 65 | 190 | 1280 | | | | | | | | | |
| 69 | 190 | 2632 | | | | | | | | | |
| 70 | 190 | 3512 | | | | | | | | | |
| 71 | 190 | 18647 | | | | | | | | | |
| 75 | 190 | 4576 | | | | | | | | | |
| 78 | 190 | 3824 | 3375 | 18175 | | | | | | | |
| 82 | 190 | 3096 | | | | | | | | | |
| 83 | 190 | 9464 | 1832 | 3144 | 2352 | 1088 | | | | | |
| 84 | 190 | 3032 | 58061 | | | | | | | | |
| 89 | 190 | 3391 | | | | | | | | | |
| 190 | 190 | 96 | 64 | 71 | 64 | 72 | 72 | 72 | 64 | 80 | 96 |
| 160 | 191 | 839 | | | | | | | | | |
| 191 | 191 | 88 | | | | | | | | | |
| 78 | 222 | 632 | 608 | | | | | | | | |
| 84 | 222 | 5655 | 792 | | | | | | | | |
| 222 | 222 | 104 | 104 | 72 | 88 | | | | | | |

APPENDIX B

June 26 1:16 pm
The Road to Newness
From Eureka Moment To Market: Bringing Ideas To Fruition The rise of the World Wide Web in the 1990s heralded an age of innovation, enabling us to make nearly every kind of interaction better, cheaper and faster.

Investors have been rewarded for funding big, game-changing ideas during this era. Yet many of these innovations have been relatively modest concepts. Being first has been key: Test your idea, fail early and pivot until you have arrived at something that captures the popular imagination.

That's no longer the case. With so much reward for low-risk ventures, fewer entities are drawn to risky investments into the unknown. But what are the subsets of creativity, and how much risk is involved in each today?

Science is the riskiest investment. The federal government has long been a consistent source of funding for scientific research, but now Congress is scaling back. Corporations can't afford to make investments that many take years, if not decades, to pay off. So science funding has become the responsibility of nonprofits, universities and a handful of extremely rich companies.

Invention is only slightly less risky than science. Inventions can sit on shelves for years until someone figures out how to use them to solve a problem in a way that consumers will buy. While there are more corporations that spend money on invention than invest in science, it is carefully controlled spending.

Innovation is the game of choice for those who want to see a quick return on their investment. Tweaking an invention to produce yet another popular product can be done so quickly that we are now in an innovation loop that no longer relies on completely new inventions to produce ever more wealth for investors. It's a spinning wheel that no longer pauses.

The glamour of innovation so outshines invention these days that inventor support groups have sprung up to champion these maligned but essential players. The Maker Movement—young inventors using inexpensive technology to make prototypes without the benefit of outside funding or the blessing of established authorities—is reinvigorating the reputation of invention.

The invention claimed is:

1. A method, comprising:
   receiving a key action data file generated from continuous typing of a document, the key action data file having a plurality of key combinations and one or more pieces of timing data about presses of the plurality of key combinations during a continuous typing sequence, wherein each key combination included in the plurality of key combinations includes a first key identifier that identifies a first key and a second key identifier that identifies a second, and wherein the key action data file is generated during a sub-clinical typing activity;
   securing the key action data file by removing an original clock stamp from each piece of timing data in the key action data file;
   determining typing cadence data from the secured key action data file, the typing cadence data including a dwell time for a first key combination when the first and second key identifiers identify a single key and a flight time between the first and second keys for a second key combination when the first and second keys are different keys;
   processing, by a processor of a backend component, the typing cadence data to generate a consistency measure by a coefficient of variance process;
   generating diagnostic data, by the processor of the backend component using the generated consistency measure, about a neurological disorder of a user; and
   generating a chart that displays the consistency measure of the user having the neurological disorder, a consistency measure of a second user that does not have a neurological disorder and an indication of a progress of the neurological disorder of the user.

2. The method of claim 1, wherein generating data about the neurological disorder further comprises determining that the neurological disorder exists in the user.

3. The method of claim 2, wherein generating data about the neurological disorder further comprises monitoring the neurological disorder in the user based on the consistency measure.

4. The method of claim 1 further comprising calculating, by the processor of the backend component using the generated consistency measure, an overall measure.

5. The method of claim 1, wherein the dwell time is a time period between pressing the first key by the user and the release of the first key by the user.

6. The method of claim 1, wherein the flight time is a time period between pressing the first key and pressing the second key.

7. The method of claim 1, wherein receiving the key action data file further comprises decrypting the key action data file.

8. The method of claim 1, wherein receiving the key action data file further comprises converting the key action data file into a spreadsheet format.

9. A method, comprising:
   providing a computing device having a processor and an input device, the computing device having a typing cadence component that is executed by the processor of the computing device;
   continuously receiving, at the input device of the computing device, data about one or more key actions on the input device generated from continuous typing of a document, the data about each key action generated during a sub-clinical typing activity and including a key combination and one or more pieces of timing data about presses of the key combination during a continuous typing sequence, wherein the key combination includes, a first key action and a second key action;
   obtaining, by the typing cadence component, the data about key actions on the input device;
   securing the key action data by removing an original clock stamp from each piece of timing data in the key action data;
   determining typing cadence data from the secured key action data;
   processing, by a processor of a backend component, the typing cadence data to generate a consistency measure by a coefficient of variance process;
   generating diagnostic data, by the processor of the backend component using the generated consistency measure, about a neurological disorder of a user; and
   generating a chart that displays the consistency measure of the user having the neurological disorder, a consistency measure of a second user that does not have a neurological disorder and an indication of a progress of the neurological disorder of the user.

10. The method of claim 9 further comprising communicating the data file to a backend system.

11. The method of claim 9, wherein obtaining the data about key actions further comprises sending the data about the key actions to an operating system of the computing device and extracting, by the typing cadence component, the data about the key actions from the data about the key actions sent to the operating system.

12. The method of claim 9, wherein generating the data file further comprises encrypting the data file.

13. The method of claim 1, wherein the neurological disorder is one of a neurological disease and a brain injury.

14. The method of claim 13, wherein the brain injury is one of a traumatic brain injury.

15. The method of claim 13, wherein the neurological disease is one of Alzheimer's, Parkinson's, multiple sclerosis, Huntington's, Lou Gehrig's disease, fronto-temporal dementia, mild cognitive impairment, HIV dementia, attention-deficit/hyperactivity disorder, post-operative neurological disorder and post-chemotherapy neurological disorder.

16. The method of claim 9, wherein the neurological disorder is one of a neurological disease and a brain injury.

17. The method of claim 16, wherein the brain injury is one of a traumatic brain injury.

18. The method of claim 16, wherein the neurological disease is one of Alzheimer's, Parkinson's, multiple sclerosis, Huntington's, Lou Gehrig's disease, fronto-temporal dementia, mild cognitive impairment, HIV dementia, attention-deficit/hyperactivity disorder, post-operative neurological disorder and post-chemotherapy neurological disorder.

* * * * *